US00PP32113P3

(12) United States Plant Patent

Lovengreen Ferreira

(10) Patent No.: US PP32,113 P3

(45) Date of Patent: Aug. 25, 2020

(54) *ARISTOTELIA* PLANT NAMED 'SOBRESALE'

(50) Latin Name: *Aristotelia chilensis*
Varietal Denomination: Sobresale

(71) Applicant: Royal Super Fruits B.V., Katwijk aan Zee (NL)

(72) Inventor: Axel Lovengreen Ferreira, Pitrufquen (CL)

(73) Assignee: ROYAL SUPER FRUITS B.V., Katwijk aan Zee (NL)

( * ) Notice: Subject to any disclaimer, the term of this patent is extended or adjusted under 35 U.S.C. 154(b) by 0 days.

(21) Appl. No.: 16/602,062

(22) Filed: Jul. 29, 2019

(65) Prior Publication Data

US 2020/0045864 P1 Feb. 6, 2020

(30) Foreign Application Priority Data

Jul. 31, 2018 (QZ) ..... PBR 2018/1993

(51) Int. Cl.

*A01H 5/00* (2018.01)
*A01H 6/00* (2018.01)
*A01H 5/12* (2018.01)

(52) U.S. Cl.

USPC ..... Plt./216
CPC ..... *A01H 6/00* (2018.05); *A01H 5/12* (2013.01)

(58) Field of Classification Search

USPC ..... Plt./216
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Aristotelia chilensis* plant named 'Sobresale' that is characterized by its vigorous plant habit, its glossy leaves that are dark green in color and its flowers that are light cream yellow to greenish yellow in color.

2 Drawing Sheets

Botanical classification: *Aristotelia chilensis*.
Varietal denomination: 'Sobresale'.

CROSS REFERENCE TO RELATED APPLICATIONS

This application is co-pending with U.S. Plant Patent Applications filed for a plant derived from the same breeding program that are entitled *Aristotelia* Plant Named 'Pretoria' (U.S. Plant patent application Ser. No. 16/602,063), *Aristotelia* Plant Named 'AZ50' (U.S. Plant patent Ser. No. 16/602,061), and *Aristotelia* Plant Named 'VB1' (U.S. Plant patent Ser. No. 16/602,064).

BACKGROUND OF THE INVENTION

The present invention relates to a new and distinct cultivar of *Aristotelia chilensis* and will be referred to hereafter by its cultivar name, 'Sobresale'. 'Sobresale' represents a perennial evergreen shrub grown for landscape use.

'Sobresale' was discovered by the Inventor as a chance seedling in a trial field in Pitrufquen, IX region de la Araucanía, Chile in January of 2013. The field had been planted with numerous unnamed proprietary seedling plants from the Inventor's breeding program. The parentage is therefore unknown.

Asexual propagation of the new cultivar was first accomplished by softwood stem cuttings by the Inventor in summer of 2014 in Pitrufquen, IX region de la Araucanía, Chile. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Sobresale' as a unique cultivar of *Aristotelia chilensis*.

1. 'Sobresale' exhibits a vigorous plant habit.
2. 'Sobresale' exhibits glossy leaves that are dark green in color.
3. 'Sobresale' exhibits flowers that are light cream yellow to greenish yellow in color.

'Sobresale' can be most closely compared to the *Aristotelia chilensis* cultivars 'Variegata' (not patented). 'Pretoria', 'AZ50', and 'VB1'. 'Variegata' differs from 'Sobresale' in having variegated foliage. 'Pretoria' differs from 'Sobresale' in having a slightly wider plant shape, more green colored young stems, green young foliage and less glossy mature foliage that is less dark green in color. 'AZ50' differs from 'Sobresale' in having a wider plant shape, less glossy foliage and lighter green foliage. 'VB1' differs from 'Sobresale' in having yellow-green branches, less glossy foliage and darker and more yellow-green mature foliage.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

BRIEF DESCRIPTION OF THE DRAWINGS

The accompanying colored photographs illustrate the overall appearance and distinct characteristics of the new

*Aristotelia.* The photographs were taken of a 24-month-old plant (with a single prune 3 weeks prior) of 'Sobresale' as grown in an unheated greenhouse in a 30-cm container in Boskoop, The Netherlands.

Figure 1:
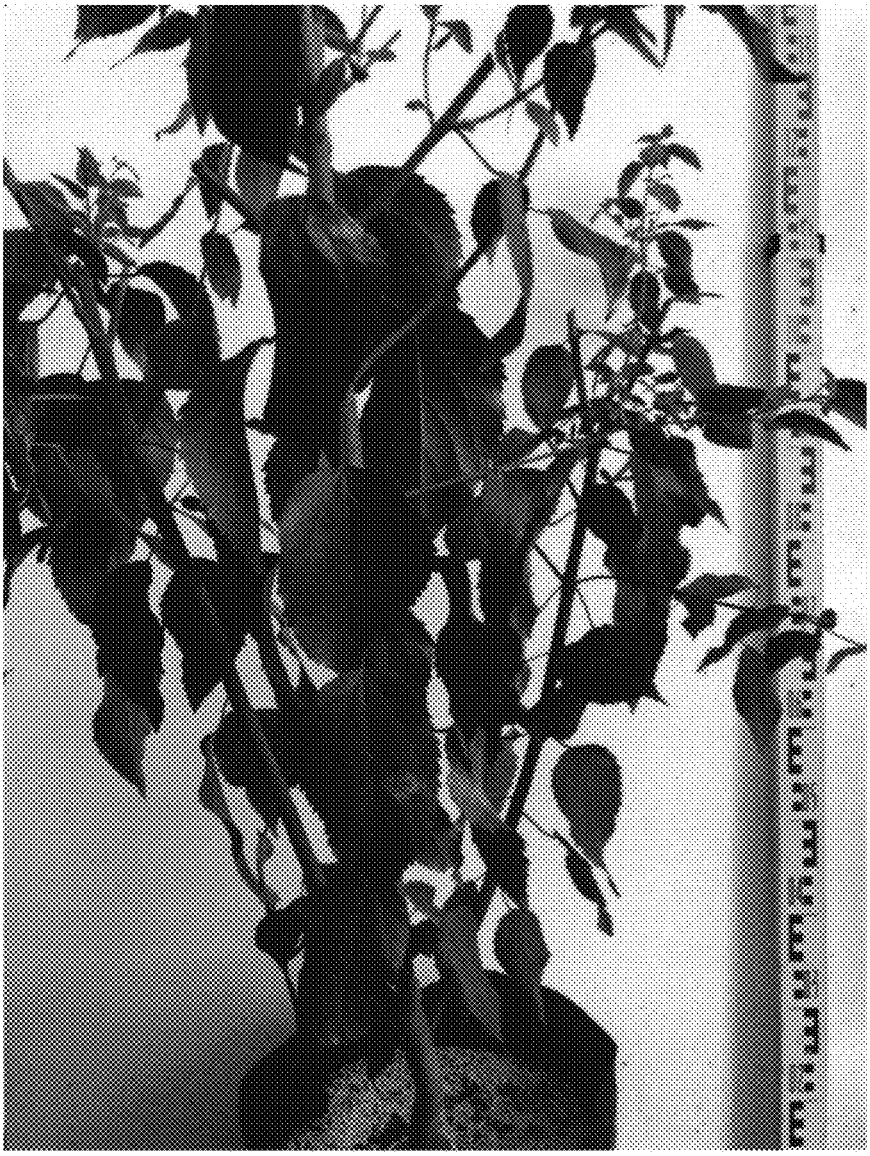

The photograph in FIG. 1 provides a view of the plant habit of 'Sobresale'.

Figure 2:
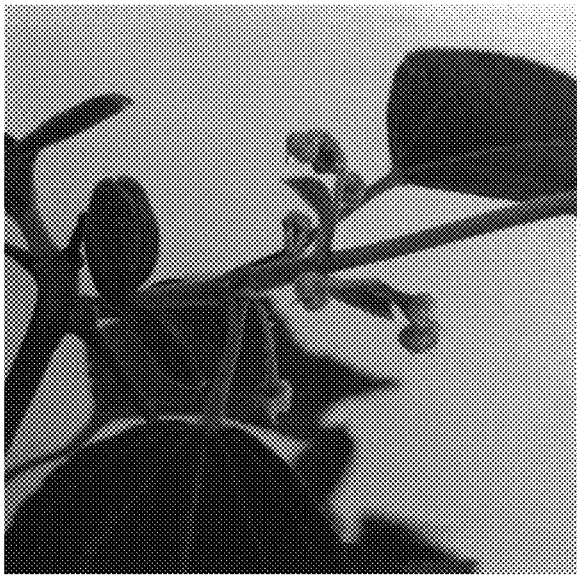

The photograph in FIG. 2. provides a close-up view of the flowers of 'Sobresale'.

Figure 3:
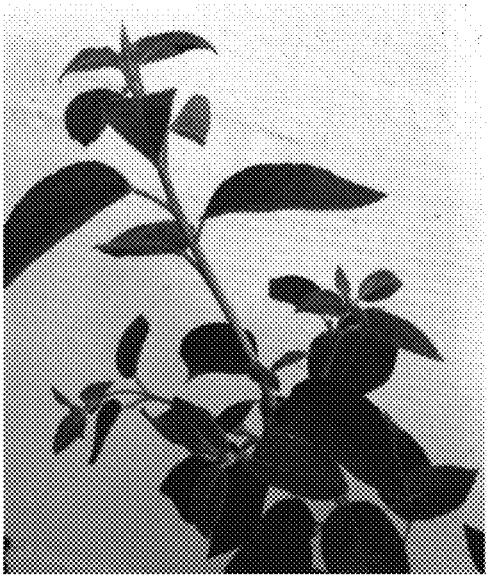

The photograph in FIG. 3 provides a close-up view of the young foliage of 'Sobresale'.

Figure 4:
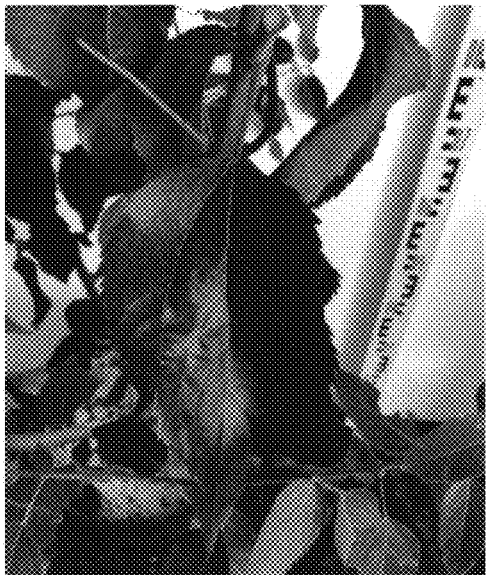

The photograph in FIG. 4 provides a close-up view of the mature foliage of 'Sobresale'.

The colors in the photographs are as close as possible with the photographic and printing technology utilized and the color values cited in the detailed botanical description accurately describe the colors of the new *Aristotelia.*

BOTANICAL DESCRIPTION OF THE PLANT

The following is a detailed description of 24-month-old plants (with a single prune 3 weeks prior) of 'Sobresale' as grown in a greenhouse in 30-cm containers in Noordwijkerhout, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type.*—Perennial, evergreen shrub.

*Plant habit.*—Obovate.

*Height and spread.*—An average of 109 cm in in height and 90.4 cm in spread, reaches 2.8 m in height and 2.5 m in spread as a mature plant in the landscape.

*Cold hardiness.*—At least in U.S.D.A. Zone 8.

*Diseases and pests.*—No susceptibility and resistance to diseases or pests has been observed.

*Root description.*—Fine and fibrous.

*Propagation.*—Softwood stem cuttings.

*Root development.*—An average of 60 days for root initiation with a young rooted plant produced in an average of 4 months.

*Growth rate and vigor.*—Vigorous.

Stem description:

*Stem shape.*—Rounded.

*Stem strength.*—Strong.

*Stem color.*—Young; 147C, mature; 146A, occasionally tinged 197A, internodes; 146A, old bark; 137A.

*Stem size.*—An average of 22.1 cm in length and 3 mm in diameter.

*Stem surface.*—Young and mature; Moderately glossy and covered with a very thin wax layer, 188A in color, old bark; densely covered with lenticels; an average of 2 mm in length, 1 mm in width and 157A in color.

*Stem aspect.*—Average angle of vertical to 35°.

*Internode length.*—An average of 5.5 cm.

*Branching.*—Freely branching with an average of 1 main branch and 24 lateral branches.

Foliage description:

*Leaf shape.*—Ovate to narrow ovate.

*Leaf arrangement.*—Opposite to near opposite.

*Leaf aspect.*—Moderately to strongly undulate.

*Leaf division.*—Simple.

*Leaf base.*—Obtuse.

*Leaf apex.*—Bluntly acute.

*Leaf margins.*—Serrate.

*Leaf venation.*—Pinnate, color; upper surface N148A, lower surface 145B to 145C.

*Leaf size.*—An average of 11.9 cm in length and 5.9 cm in width.

*Leaf attachment.*—Petiolate.

*Leaf number.*—An average of 10 (5 pairs).

*Leaf surface.*—Upper surface; glossy and glabrous and slightly rugose, lower surface; smooth, glabrous and slightly rugose with small tufts on the vein axils, 156D in color.

*Leaf color.*—Young foliage; upper surface 146A, changing to 152A at the margins, young lower surface 146A, mature foliage; upper surface acolor between 139A and N189A, mature lower surface 137B and 147B.

*Petioles.*—An average of 2.5 cm in length and 1.5 mm in diameter, strong, upper surface color 178A, lower surface color 144B to 144C and slightly tinged with 178B, both surfaces matte, smooth and glabrous and moderately pubescent; an average of 0.2 mm in length and too small to measure color.

Inflorescence description:

*Blooming period.*—An average of 4 weeks in spring in Chile.

*Inflorescence type.*—Solitary or in pairs.

*Lastingness of flowers.*—Average of one week, self-cleaning.

*Flower number.*—An average of 1 to 2 per inflorescence, 23 flowers and buds per plant.

*Flower fragrance.*—None.

*Flower aspect.*—Nodding.

*Flower type.*—Rotate.

*Flower size.*—Average of 3 mm in height and diameter and 3.5 mm in depth.

*Flower buds.*—Average of 2 mm in length and diameter, globular in shape, matte surface, 143C in color, moderately to densely pubescent average of 0.2 mm in length and too small to measure color.

*Peduncles.*—Moderately strong, average of 9 mm in length and 1 mm in diameter, held at 70°, 143C in color, surface matte and moderately pubescent with hairs 0.2 mm in length and too small to measure color.

*Pedicels.*—Moderately strong, average of 4 mm in length, 0.75 mm in diameter, held at 25°, 143C in color, surface matte and moderately pubescent with hairs 0.2 mm in length and too small to measure color.

*Petals.*—Rotate, 5, 1 whorl, 2.75 mm in length, 1.75 mm in width, obcordate and slightly concave in shape, retuse to broadly emarginate apex, cuneate base, entire margins, both surfaces glabrous, slightly velvety and matte, color; when opening upper and lower surface 145B to 145C, when fully open upper and lower surface 150D, changing to 154C to 154D at the base.

*Calyx.*—Rotate, cup-shaped, 2.5 mm in length and 3 mm in diameter.

*Sepals.*—Rotate, 6, 1 whorl, 2 mm in length, 1 mm in width, ovate in shape, acute apex, broad cuneate base, entire margins, color; when opening upper and lower surface 150B, when fully open upper and lower surface 145C, both surfaces smooth and matte, lower surface densely pubescent with hairs 0.2 mm in length and too small to measure color.

Reproductive organs:

*Gynoecium.*—Pistils; 3, an average of 1 mm in length, stigma; club-shaped, 0.3 mm in length and diameter and 145B in color, style; 0.7 mm in length, 145B in color, ovary is 145A in color.

*Androecium.*—Stamens; average of 15, filaments; an average of 0.5 mm in length and 151C in color, anthers; short oblong in shape, an average of 1 mm in length, 0.5 mm in width, 151B to 151C in color, pollen; high in quantity, 155B in color.

*Fruit and seed.*—No production observed to date on plants available for data collection.

It is claimed:

1. A new and distinct cultivar of *Aristotelia* plant named 'Sobresale' substantially as herein illustrated and described.

* * * * *